United States Patent
Cabri et al.

(10) Patent No.: US 8,530,517 B2
(45) Date of Patent: Sep. 10, 2013

(54) RETINOID DERIVATIVES ENDOWED WITH CYTOTOXIC AND/OR ANTIANGIOGENIC PROPERTIES

(75) Inventors: Walter Cabri, Rozzano (IT); Giuseppe Giannini, Pomezia (IT); Gianfranco Battistuzzi, Rome (IT); Domenico Alloatti, Rome (IT); Claudio Pisano, Aprilia (IT); Sabrina Dallavalle, Vimercate (IT); Tiziana Brunetti, Pomezia (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 13/141,831

(22) PCT Filed: Dec. 21, 2009

(86) PCT No.: PCT/EP2009/067667
§ 371 (c)(1),
(2), (4) Date: Aug. 29, 2011

(87) PCT Pub. No.: WO03/011808
PCT Pub. Date: Feb. 13, 2003

(65) Prior Publication Data
US 2011/0312965 A1 Dec. 22, 2011

(30) Foreign Application Priority Data
Dec. 24, 2008 (EP) .................................... 08172883

(51) Int. Cl.
*A61K 31/192* (2006.01)
*C07C 235/32* (2006.01)
(52) U.S. Cl.
USPC .......................................... 514/568; 560/102
(58) Field of Classification Search
USPC .......................................... 560/102; 514/568
See application file for complete search history.

(56) References Cited

FOREIGN PATENT DOCUMENTS
WO    WO 2007/000383    1/2007
WO    WO 03/011808      2/2008

OTHER PUBLICATIONS

Di Francesco et al, "The novel atypical retinoid ST1926 is activei in ATRA resistant neuroblastoma cells acting by a different mechanism," Biochemical Pharmacology 73(2007), pp. 643-655.*
Cincinelli, et al., Synthesis and Structure-Activity Relationships of New Antiproliferative and Proapoptotic Retinoid-Related Biphenyl-4-yl-Acrylic Acids, Bioorganic & Medicinal Chemistry (2007) vol. 15, p. 4863-4875.
Cincinelli, et al., Synthesis and Structure-Activity Relationships of a New Series of Retinoid-Related Biphenyl-4-ylacrylic Acids Endowed With Antiproliferative and Proapoptotic Activity, J. Med. Chemistry (2005) vol. 48, p. 4931-4946.
DiFrancesco, et al., The Novel Atypical Retinoid ST1926 is Active in ATRA Resistant Neuroblastoma Cells Acting by a Different Mechanism, Biochemical Pharmacology (2007) vol. 73, p. 643-655.
Aurelio C . Csáky, et al., Asymmetric C—C Bond Formation By The Mixed Oxidative Coupling Of 1,1'-Bi-2-Naphthyl Esters, Tetrahedron: Asymmetry (2002) vol. 13, pp. 753-757.

* cited by examiner

*Primary Examiner* — Kamal Saeed
*Assistant Examiner* — Janet L Coppins
(74) *Attorney, Agent, or Firm* — Vedder Price P.C.; Thomas J. Kowalski; Samuel Megerditchian

(57) ABSTRACT

The present invention relates to new retinoid derivatives of formula I and to pharmaceutical compositions containing them for the treatment of patients affected by pathologies such as arthritic conditions, tumors, metastatic cancer, diabetic retinopathy, psoriasis, chronic inflammatory diseases or atherosclerosis.

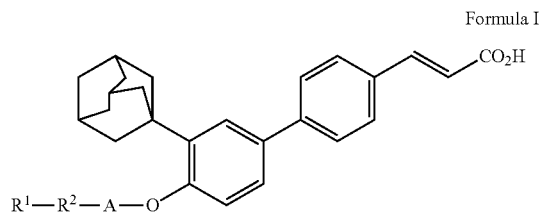

Formula I

15 Claims, No Drawings

RETINOID DERIVATIVES ENDOWED WITH CYTOTOXIC AND/OR ANTIANGIOGENIC PROPERTIES

CROSS REFERENCE TO RELATED APPLICATIONS

This application is a National Stage filing under 35 U.S.C. §371 of PCT Application No. PCT/EP2009/067667, filed Dec. 21, 2009, and published as WO 2010/072727 on Jul. 1, 2010, which claims priority to application Serial No. EP 08172883.4, filed Dec. 24, 2008.

FIELD OF THE INVENTION

The present invention relates to new cytotoxic agents and compositions thereof.

BACKGROUND OF THE INVENTION

The term "retinoid" is commonly used to define vitamin A analogues that bind to nuclear retinoid receptors; retinoic acid receptors (RAR) and retinoid X receptors (RXR). Once the retinoid derivative is coupled to the receptors, the latter form homo- or heterodimers, and through binding to the response element (RARE or RXRE) upstream of the target gene, regulates the gene expression as a transcriptional factor influencing cellular differentiation, tissue morphogenesis and programmed cell death. As a consequence, retinoid derivatives are promising compounds to prevent and/or treat cancers of various organs.

WO03/011808 filed in the name of the Applicant, describes retinoid derivatives endowed with antiangiogenic, antitumoral and pro-apoptotic activities. ST1926 (adarotene, example 4 of the above application) belongs to a so-called class of atypical retinoids and was found to be a potent pro-apoptotic agent for the treatment of neoplastic diseases. More recently, the same Applicant filed an international application dealing with the combination between a retinoid derivative and a platinum anticancer agent (WO08/077772).

The Applicant also filed an application (WO07/071605) concerning the use of a 4-O-methyl analogue of adarotene (ST1898) for the preparation of a medicament for treating pathological states, which arise from a complex series of cellular responses to vascular injury.

Dawson M. I., et al., recently published a pharmacophore model related to 4-[3'-(1-adamantyl)-4'-hydroxyphenyl]-3-chlorocinnamic acid, based on QSAR analyses relating the polar termini with cancer cell growth inhibition (Dawson M. I., et al., *J. Med. Chem.*, 2007, 50, 2622). A further study from the same authors reveals an important interaction between the H atom of the 4'-OH of the retinoid derivative and the side chain of the residue Phe-96 of the small heterodimer partner through hydrogen-Π interaction thus stabilizing the complex (Dawson M I., et al., *J. Med. Chem.*, 2008, 51, 5650).

In WO07/000383, the Applicant reported the cytotoxicity activity of retinoid derivatives against NCI H460 tumour cells. 4'-OH retinoid adduct (ST1926) showed an $IC_{50}$ value a log unit lower than that of its 4'-OMe analogue (ST1898).

The same Applicant also reported the antiproliferative activity of, among others the above two compounds (ST1926 and its methylated analogue ST1898) on IGROV-1, IGROV-1/Pt1, and NB4 cellular lines (Cincinelli R., et al., *Bioorg. Med. Chem.*, 2007, 15, 4863). Those results, as already demonstrated on different cell lines reveal that the 4'-OH retinoid compound is more active than its 4'-OMe counterpart.

It is well known to those skilled in the art that a major mechanism of elimination of drugs from the body stream occurs through glucuronidation favouring excretion by the urines. It has been reported that that retinoyl β-glucuronide is synthesized rapidly from orally administered all-trans retinoic acid and can be detected in the blood within 30 min after the administration of retinoic acid (Barua A B., et al., *Biochem. J.*, 1991, 277, 527). It is also well known that phenol derivatives can be substrate of UDP-glucuronosyltransferases (Ethell T. B., et al., *Drug Metab. and Depos.*, 2002, 30, 6, 734).

Despite the many efforts over the past decades aimed at finding new and more potent retinoid derivatives endowed with antiangiogenic, antitumoral and/or pro-apoptotic activities, there is still a strong medical need of more adequate medicaments.

DESCRIPTION OF THE INVENTION

The invention provides compounds of formula (I) or a salt, hydrate or solvate thereof, in the preparation of a composition endowed with antiangiogenic, antitumoral and pro-apoptotic activities:

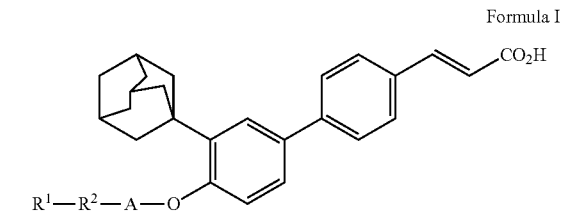

Formula I

Wherein
$R^1$ is H, O(CO)OR$^4$, NR$^4$R$^5$, CN, alkyl, cycloalkyl or heterocycloalkyl; wherein alkyl, cycloalkyl and heterocycloalkyl are optionally substituted once or more with $C_1$-$C_6$ alkyl, $(CH_2)_n COR^3$, O(CO)OR$^4$, OH or NR$^4$R$^5$;
n is 0 or 1;
$R^3$ is OH, amino, ($C_1$-$C_3$)-alkyl-amino or benzyloxy;
$R^4$ and $R^5$, the same or different are H, alkyl; or
$R^4$ and $R^5$ taken together with the nitrogen atom to which they are attached form a heterocycloalkyl group; or
NR$^4$R$^5$ form a nitro group;
$R^2$ is alkylene, hydroxyalkylene, aminocarbonylalkylene, ($C_2$-$C_{18}$)-alkenylene, ($C_3$-$C_6$)-cycloalkylene, heterocycloalkylene, —(OCH$_2$CH$_2$)$_m$—O—, branched or linear polyaminoalkylene, phenyloxy optionally substituted with NO$_2$; or is absent;
m is an integer comprised between 1 and 4;
A is CH$_2$—, —CO—, —CH$_2$—(CO)—, —NH(CO)— or —[CO—(CHR$^6$)—NH]$_w$;
$R^6$ is the side chain of a natural amino acid radical;
w is 1;
their tautomers, their geometrical isomers, their optically active forms such as enantiomers, diastereomers and their racemate forms, as well as their pharmaceutically acceptable salts thereof;
with the proviso that R$^1$-R$^2$-A does not represent alkyl or alkyl-CO.

We have found that the derivatives (I) and their pharmaceutically acceptable salts, prepared according to the invention, are useful agents for the treatment of disease states, disorders and pathological conditions related to altered angiogenesis.

An embodiment of this invention is that of compounds of formula I, for use as medicaments.

In another embodiment, said medicament is used for treating a subject affected by arthritic conditions, neoplasms, diabetic retinopathy, psoriasis, chronic inflammatory diseases or arthritis.

The term "neoplasm" indicates an abnormal mass of tissue as a result of neoplasia. Neoplasia is the abnormal proliferation of cells. The growth of this clone of cells exceeds, and is uncoordinated with, that of the normal tissues around it. It usually causes a tumour. Neoplasms may be benign, pre-malignant or malignant. Benign neoplasms include for example uterine fibroids and melanocytic nevi and do not transform into cancer. Potentially malignant neoplasms include carcinoma in situ. They do not invade and destroy the surrounding tissue but, given enough time, will transform into a cancer. Malignant neoplasms are commonly called cancer. They invade and destroy the surrounding tissue, may form metastases and eventually kill the host.

Metastasis is the spread of a disease from one organ or part to another non-adjacent organ or part. Only malignant tumour cells and infections have the established capacity to metastasize.

Cancer cells can break away, leak, or spill from a primary tumour, enter lymphatic and blood vessels, circulate through the bloodstream, and be deposited within normal tissues elsewhere in the body. Metastasis is one of three hallmarks of malignancy. Most tumours can metastasize, although in varying degrees (e.g., glioma and basal cell carcinoma rarely metastasize). When tumour cells metastasize, the new tumour is called a secondary or metastatic tumour, and its cells are like those in the original tumour.

According to an embodiment of the present invention the neoplasm to be treated is a primary tumour.

According to a further embodiment of the present invention the neoplasm to be treated is a malignant neoplasm, also called cancer, or a potentially malignant neoplasm.

A further embodiment of the present invention is related to the use of compounds of formula I for the preparation of a medicament useful in the treatment of tumours wherein the antitumoural activity is derived from the cytotoxic, and/or apoptotic, and/or antiangiogenic properties of compounds of formula I.

A still further embodiment of the present invention is related to the use of compounds of formula I wherein the tumour is selected from the group comprising sarcoma, carcinoma, melanoma, bone tumour, neuroendocrine tumour, lymphoid leukaemia, myeloid leukaemia, monocytic leukaemia, megakaryocytic leukaemia, acute promyelocytic leukaemia or Hodgkin's disease.

In a still further embodiment of the present invention, the above mentioned sarcoma and carcinoma consist of the group comprising: breast cancer; lung cancer, including non-small cell lung cancer (NSCLC) and small-cell lung cancer (SCLC); gastrointestinal cancer, including esophageal, gastric, small bowel, large bowel, rectal and colon cancer; glioma, including glioblastoma; ovarian cancer, cervical cancer, endometrial cancer, mesothelioma; renal cancer; prostate cancer and skin cancers.

The present invention also relates to the treatment of paediatric cancers.

For example paediatric cancers that can be treated or where the progression of the condition can be delayed according to the present invention are selected from the group consisting of: acute lymphoblastic leukaemia, acute myeloid leukaemia, adrenocortical carcinoma, astrocytomas, bladder cancer, brain stem glioma, central nervous system atypical teratoid/rhabdoid cancer, brain cancer, central nervous system embryonal cancers, brain cancer, astrocytomas, craniopharyngioma, ependymoblastoma, ependymoma, childhood medulloblastoma, medulloepithelioma, pineal parenchymal cancers of intermediate differentiation, supratentorial primitive neuroectodermal cancers and pineoblastoma, breast cancer, bronchial cancers, carcinoid cancer, cervical cancer, chordoma, colorectal cancer, oesophageal cancer, extra cranial germ cell cancer, gastric cancer, glioma, hepatocellular (liver) cancer, Hodgkin lymphoma, kidney cancer, laryngeal cancer, leukaemia, acute lymphoblastic/myeloid leukaemia, liver cancer, non-Hodgkin lymphoma, medulloblastoma, mesothelioma, multiple endocrine neoplasia syndrome, nasopharyngeal cancer, oral cancer, ovarian cancer, pancreatic cancer, papillomatosis, renal cell cancer, rhabdomyosarcoma, salivary gland cancer, sarcoma, skin cancer, thymoma and thymic carcinoma, thyroid cancer and vaginal cancer.

A still further embodiment of the present invention is related to the use of compounds of formula I for the preparation of a medicament useful in the treatment of tumour metastasis of the above mentioned tumour types.

The invention furthermore provides a process for the preparation of compounds of formula I, which can be prepared by conventional synthetic methods and are described underneath.

Compounds of formula I, where A represents —CO—, —CH$_2$—(CO)— or —[CO(CHR$^6$)—NH]$_w$, wherein R$^6$ and w are as defined above and R$^1$ and R$^2$ are as defined above can be obtained by reacting E-4-(3-(1-adamantyl)-4-hydroxyphenyl)cinnamic acid (described in WO03/011808, example 4) with a compound of formula R$^7$—(CO)—Cl (formula II), wherein R$^7$—(CO) has the meaning of R$^1$-R$^2$-A, in an aprotic solvent such as for example THF or DCM in the presence of a base such as for example DIPEA or NEt$_3$ at a temperature ranging from 0° C. to RT. Alternatively, such compounds can be obtained by standard esterification procedures well-known to those skilled in the art, by reacting E-4-(3-(1-adamantyl)-4-hydroxyphenyl)cinnamic acid with an acid of formula R$^7$(CO)—OH (formula III), wherein R$^7$—(CO) has the meaning of R$^1$-R$^2$-A, in the presence of a coupling agent such as PyBop, HATU, DCC and of a base such as DIPEA or NEt$_3$ in an aprotic solvent such as for example THF or DCM at a temperature ranging from 0° C. to RT followed by subsequent cleavage of the formed mixed anhydride. Alternatively, the latter coupling can be performed by using tert-butyl E-3-(3'-adamantan-1-yl-4'-hydroxybiphenyl-4-yl) acrylate instead of E-4-(3-(1-adamantyl)-4-hydroxyphenyl) cinnamic acid, followed by subsequent cleavage of the tert-butyl ester by means of TFA.

Compounds of formula I, where R$^1$-R$^2$-A represents a group of formula R$^1$—R$^2$—NH—(CO)—, where R$^1$ and R$^2$ are as defined above, can be obtained by reacting E-4-(3-(1-adamantyl)-4-hydroxyphenyl)cinnamic acid with a compound of formula R$^1$—R$^2$—NCO (formula IV), in an aprotic solvent such as for example Et$_2$O or DCM in the presence of a base such as for example NEt$_3$ or pyridine. Alternatively, such compounds can be obtained by reacting tert-butyl E-3-(3'-adamantan-1-yl-4'-hydroxybiphenyl-4-yl)acrylate with a compound of formula R$^1$-R$^2$-NHCOCl (formula V) in the presence of a base such as for example DIPEA or NEt$_3$ in a solvent such as for example DCM, followed by subsequent cleavage of the tert-butyl ester by means of TFA.

Compounds of formula I, where R$^1$ is heterocycle, R$^2$ is phenyloxy optionally substituted with NO$_2$ and A is —CH$_2$— can be obtained as described by Leu Y. L., et al. (Leu Y. L., et al., *J. Med. Chem.*, 2008, 51, 1740) starting from tert-butyl E-3-(3'-adamantan-1-yl-4'-hydroxybiphenyl-4-yl)acrylate, followed by subsequent cleavage of the tert-butyl ester by means of TFA.

In all said transformations, any interfering reactive group can be protected and then deprotected according to well-established procedures described in organic chemistry (see for example: Greene T. W. and P. G. M. Wuts "Protective Groups in Organic Synthesis", J. Wiley & Sons, Inc., 3rd Ed., 1999) and well known to those skilled in the art.

All said transformations are only examples of well-established procedures described in organic chemistry (see for example: March J., "Advanced Organic Chemistry", J. Wiley & Sons, Inc., 4th Ed., 1992) and well known to those skilled in the art.

The term "alkyl" refers to linear or branched alkyl groups having from 1 to 20 carbon atoms, or preferably, 1 to 12 carbon atoms.

The term alkylene, either alone or when part of a more complex structure (e.g. heterocycloalkylene) represents an alkyl radical which can be divalent.

The term "polyaminoalkyl" refers to an alkyl group, which chain is interrupted by one or more nitrogen atom.

The term "cycloalkyl" refers to a saturated or partially unsaturated (but not aromatic) carbocyclic group of 3 to 10 carbon atoms having a single ring or multiple condensed rings. Examples of "$C_3$-$C_{10}$-cycloalkyl" include cyclopropyl, cyclobutyl, cyclopentyl, cyclohexyl, norbornyl, adamantyl and the like.

The terms "heterocycloalkyl" and heterocycle refer to a saturated or partially unsaturated (but not aromatic) five-, six- or seven-membered ring containing one or two nitrogen, oxygen or sulfur atoms, which may be the same or different and which rings may be substituted with one o more groups selected from hydroxyl and carboxyl. Preferred heterocycloalkyl include pyrrolidine, piperidine, piperazine, morpholine, tetrahydropyran and phtalimide.

The term "natural amino acid radical" refers to any natural amino acid selected from the group consisting of glycine, alanine, phenylalanine, valine, leucine, isoleucine, aspartic acid, asparagine, glutamic acid, glutamine, serine, lysine, histidine, methionine, proline, cysteine, threonine, tryptophan, arginine, tyrosine, and γ-aminobutyric acid.

The term "amino" refers to a group NRR' wherein each R and R' are H or alkyl.

The term "aminocarbonylalkyl" refers to an alkyl group substituted by an aminocarbonyl moiety.

The term "aminocarbonyl" refers to a group of formula —NRR'CO— wherein each R and R' are H or alkyl.

Another embodiment of the present invention is related to a pharmaceutical composition containing at least one compound of formula I as an active ingredient, in an amount such as to produce a significant therapeutic effect.

The compositions covered by the present invention are entirely conventional and are obtained with methods which are common practice in the pharmaceutical industry, such as, for example, those illustrated in Remington's Pharmaceutical Science Handbook, Mack Pub. N.Y.—last edition. According to the administration route chosen, the compositions will be in solid or liquid form, suitable for oral, parenteral or topical administration. The compositions according to the present invention contain, along with the active ingredient, at least one pharmaceutically acceptable vehicle or excipient. These may be particularly useful formulation coadjuvants, e.g. solubilising agents, dispersing agents, suspension agents, and emulsifying agents.

Generally, the compounds of this invention are administered in a "therapeutically effective amount". The amount of the compound actually administered will typically be determined by a physician, in the light of the relevant circumstances, including the condition to be treated, the chosen route of administration, the actual compound administered, drug combination, the age, body weight, and response of the individual patient, the severity of the patient's symptoms, and the like. For any compound, the therapeutically effective dose can be estimated initially either in cell culture assays or in animal models, usually mice, rats, guinea pigs, rabbits, dogs, or pigs. The animal model may also be used to determine the appropriate concentration range and route of administration. Such information can then be used to determine useful doses and routes for administration in humans. In calculating the Human Equivalent Dose (HED) it is recommended to use the conversion table provided in Guidance for Industry and Reviewers document (2002, U.S. Food and Drug Administration, Rockville, Md., USA).

Generally, an effective dose will be from 0.01 mg/kg to 100 mg/kg, preferably 0.05 mg/kg to 50 mg/kg. For any compound, the therapeutically effective dose can be estimated initially either in cell culture assays or in animal models, usually mice, rats, guinea pigs, rabbits, dogs, or pigs. The precise effective dose for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician.

Compositions may be administered individually to a patient or may be administered in combination with other agents, drugs or hormones.

The medicament may also contain a pharmaceutically acceptable carrier, for administration of a therapeutic agent. Such carriers include antibodies and other polypeptides, genes and other therapeutic agents such as liposomes, provided that the carrier does not induce the production of antibodies harmful to the individual receiving the composition, and which may be administered without undue toxicity.

Suitable carriers may be large, slowly metabolised macromolecules such as proteins, polysaccharides, polylactic acids, polyglycolic acids, polymeric amino acids, amino acid copolymers and inactive virus particles.

A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol.

Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The medicament of this invention may be administered by any number of routes including, but not limited to, oral, intravenous, intramuscular, intra-arterial, intramedullary, intrathecal, intraventricular, transdermal or transcutaneous applications, subcutaneous, intraperitoneal, intranasal, enteral, topical, sublingual, intravaginal or rectal means.

The compositions for oral administration may take the form of bulk liquid solutions or suspensions, or bulk powders.

More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include refilled, pre-measured ampoules or syringes of the liquid compositions or pills, tablets, capsules or the like in the case of solid compositions. In such compositions, the compound of the invention is usually a minor component (from about 0.1 to about 50% by weight or preferably from about 1 to about 40% by weight) with the remainder being various vehicles or carriers and processing aids helpful for forming the desired dosing form. Dosage treatment may be a single dose schedule or a multiple dose schedule.

Objects of the present invention are pharmaceutical compositions containing one or more of the compounds of formula (I) described earlier, in combination with excipients and/or pharmacologically acceptable diluents.

The compositions in question may, together with the compounds of formula (I), contain further known active principles.

A further object of the invention is a process for the preparation of pharmaceutical compositions characterised by mixing one or more compounds of formula (I) with suitable excipients, stabilizers and/or pharmaceutically acceptable diluents.

An embodiment of this invention is that of compounds of formula (I) described earlier, wherein A is —CO—.

A further embodiment of this invention is that of compounds of formula (I) described earlier, wherein $R^1$ is cycloalkyl optionally substituted with amino.

Another further embodiment of this invention is that of compounds of formula (I) described earlier, wherein A is —CH$_2$—(CO)—.

A still further embodiment of this invention is that of compounds of formula (I) described earlier, wherein $R^2$ is —(OCH$_2$CH$_2$)$_m$—O— and $R^1$ is —(CH$_2$)$_n$COR$^3$.

Another still further embodiment of this invention is that of compounds of formula (I) described earlier, wherein A is CH$_2$ and $R^1$ is O(CO)OR$^4$.

Another still further embodiment of this invention is that of compounds of formula (I) described earlier, wherein A is —[CO(CHR$^6$)—NH]$_w$—.

A preferred embodiment of this invention is that of compounds of formula (I) described earlier, wherein A is —[CO(CHR$^6$)—NH]$_w$—, wherein w is preferably the integer 1 or 2.

Another still further embodiment of this invention is that of compounds of formula (I) described earlier, wherein $R^1$ represents a heterocycloalkyl and $R^2$ represents alkylene.

A more preferred embodiment of the present invention consists of the compounds selected from the group consisting of (S)-2-amino-3-methyl-butyric acid 3-adamantan-1-yl-4'-((E)-2-carboxy-vinyl)-biphenyl-4-yl ester hydrochloride; (E)-3-(3'-adamantan-1-yl-4'-{2-[2-(2-carboxymethoxy-ethoxy)-ethoxy]-acetoxy}-biphenyl-4-yl)-acrylic acid; undecanoic acid 3-adamantan-1-yl-4'-(E)-2-carboxy-vinyl)-biphenyl-4-yl ester; 4-morpholin-4-yl-butyric acid 3-adamantan-1-yl-4'-((E)-2-carboxy-vinyl)-biphenyl-4-yl ester hydrochloride; 4-(4-methyl-piperazin-1-yl)-butyric acid 3-adamantan-1-yl-4'-((E)-2-carboxy-vinyl)-biphenyl-4-yl ester dihydrochloride; (E)-3-[3'-adamantan-1-yl-4'-(2-methylamino-ethylcarbamoyloxy)-biphenyl-4-yl]-acrylic acid; (E)-3-(3'-adamantan-1-yl-4'-carboxymethylcarbamoyloxy-biphenyl-4-yl)-acrylic acid; (E)-3-[3'-adamantan-1-yl-4'-(4-amino-butylcarbamoyloxy)-biphenyl-4-yl]-acrylic acid hydrochloride; (E)-3-[3'-adamantan-1-yl-4'-(2-morpholin-4-yl-ethyl-carbamoyloxy)-biphenyl-4-yl]-acrylic acid hydrochloride; (E)-3-(3'-adamantan-1-yl-4'-undecyl-carbamoyloxy-biphenyl-4-yl)-acrylic acid; [1,4']bipiperidinyl-1'-carboxylic acid 3-adamantan-1-yl-4'-((E)-2-carboxy-vinyl)-biphenyl-4-yl ester hydrochloride; (E)-3-(3'-adamantan-1-yl-4'-isopropylcarbamoyloxy-biphenyl-4-yl)-acrylic acid; 4-[3-adamantan-1-yl-4'-((E)-2-carboxy-vinyl)-biphenyl-4-yloxycarbonylamino]-piperidine-1-carboxylic acid benzyl ester; (E)-3-{3'-adamantan-1-yl-4'-[(S)-1-(carboxymethyl-carbamoyl)-2-methyl-propylcarbamoyloxy]-biphenyl-4-yl}-acrylic acid; (E)-3-[3+-adamantan-1-yl-4'-(2-methoxy-ethoxymethoxy)-biphenyl-4-yl]-acrylic acid; cyclopropanecarboxylic acid 3-adamantan-1-yl-4'-((E)-2-carboxy-vinyl)-biphenyl-4-yl ester; E)-3-[3'-adamantan-1-yl-4'-(1,3-dioxo-1,3-dihydro-isoindol-2-ylmethoxy)-biphenyl-4-yl]-acrylic acid; (9Z,12E)-octadeca-9,12-dienoic acid 3-adamantan-1-yl-4'-((E)-2-carboxy-vinyl)-biphenyl-4-yl ester; (E)-3-(3'-adamantan-1-yl-4'-propoxycarbonyloxymethoxy-biphenyl-4-yl)-acrylic acid; 1-amino-cyclopropanecarboxylic acid 3-adamantan-1-yl-4'-((E)-2-carboxy-vinyl)-biphenyl-4-yl ester; (E)-3-(3'-adamantan-1-yl-4'-cyanomethoxy-biphenyl-4-yl)-acrylic acid; (E)-3-(3'-adamantan-1-yl-4'-carbamoylmethoxy-biphenyl-4-yl)-acrylic acid and (E)-3-[3'-adamantan-1-yl-4'-(2-morpholin-4-yl-ethoxy)-biphenyl-4-yl]-acrylic acid.

An even more preferred embodiment of the present invention consists of the compounds selected from the group consisting of: (S)-2-amino-3-methyl-butyric acid 3-adamantan-1-yl-4'-((E)-2-carboxy-vinyl)-biphenyl-4-yl ester hydrochloride; (E)-3-(3'-adamantan-1-yl-4'-{2-[2-(2-carboxymethoxy-ethoxy)-ethoxy]-acetoxy}-biphenyl-4-yl)-acrylic acid; 4-morpholin-4-yl-butyric acid 3-adamantan-1-yl-4'((E)-2-carboxy-vinyl)-biphenyl-4-yl ester hydrochloride; 4-(4-methyl-piperazin-1-yl)-butyric acid 3-adamantan-1-yl-4'-((E)-2-carboxy-vinyl)-biphenyl-4-yl ester dihydrochloride; (E)-3-[3'-adamantan-1-yl-4'-(2-methylamino-ethylcarbamoyloxy)-biphenyl-4-yl]-acrylic acid; (E)-3-[3'-adamantan-1-yl-4'-(2-morpholin-4-yl-ethyl-carbamoyloxy)-biphenyl-4-yl]-acrylic acid hydrochloride; cyclopropanecarboxylic acid 3-adamantan-1-yl-4'-((E)-2-carboxy-vinyl)-biphenyl-4-yl ester; (E)-3-(3'-adamantan-1-yl-4-propoxycarbonyloxymethoxy-biphenyl-4-yl)-acrylic acid; 1-aminocyclopropanecarboxylic acid 3-adamantan-1-yl-4'-((E)-2-carboxy-vinyl)-biphenyl-4-yl ester and (E)-3-(3'-adamantan-1-yl-4'-cyanomethoxy-biphenyl-4-yl)-acrylic acid.

The following examples further illustrate the invention, without limiting it.

EXAMPLES

Abbreviations:
EtOAc: ethyl acetate
bm: broad multiplet
Boc: tert-Butoxycarbonyl
bs: broad singlet
DCM: dichloromethane
dd: doublet of doublet
DIPEA: diisopropylethylamine
DMF: dimethylformamide
DMSO: dimethylsulfoxide
Et$_2$O: diethyl ether
MeCN: acetonitrile
MEM-Cl: methoxyethoxymethyl chloride
MeOH: methanol Na$_2$SO$_4$: sodium sulfate
NMP: N-methyl pyrrolidinone
PyBop: (benzotriazol-1-yloxy)tripyrrolidinophosphonium hexafluorophosphate
RP-HPLC: reversed phase-high-performance liquid chromatography
RT: room temperature
TBDPSiCl: tert-butyldiphenylsilyl chloride
TCA: trichloroacetic acid
TFA: trifluoroacetic acid
TLC: thin-layer chromatography General Remarks Reactions and product mixtures were routinely monitored by TLC on silica gel F$_{254}$ Merck plates. Flash column chromatography was carried out using silica gel (Merck 230-400 mesh). Nuclear magnetic resonance ($^1$H and $^{13}$C NMR) spectra were gathered, with a Bruker AC-200 spectrometer or with a Varian Mercury Plus 400, and chemical shifts are given in part per million (ppm) downfield from tetramethylsilane as internal standard. The coupling constants are given in Hz. Mass spectra were obtained with an ESI MICROMASS ZMD2000.

All drying operations were performed over anhydrous sodium sulphate. Flash column chromatography (medium pressure) was carried out using silica gel (Merck 230-400 mesh). Yields are given after purification.

Preparation 1

(E)-3-(3'-adamantan-1-yl-4'-hydroxy-biphenyl-4-yl)-acrylic acid tert-butyl ester ST5763AA1

Pd(OAc)$_2$ (6.7 mg, 0.03 mmol) was added into a flask containing a mixture of 3-adamantan-1-yl-4'-bromo-biphenyl-4-ol (1.15 g, 2.99 mmol), tert-butyl acrylate (1.75 g, 11.96 mmol), NEt$_3$ (1.25 ml, 8.97 mmol), tetrabutylammonium chloride (1.329 g, 4.78 mmol) and NMP (3 ml). The flask, equipped with a glycol-cooled condenser, was immerged in a pre-heated oil bath (110° C.) and the reaction mixture was stirred at this temperature overnight. The mixture was allowed to return to RT and was diluted with DCM and washed with H$_2$O. The organic phase was dried over Na$_2$SO$_4$ and the solvent was removed under reduced pressure. The crude reaction mixture was taken-up in dioxane (10 ml) and the resulting solution added dropwise to 40 ml of H$_2$O. The suspension was then sonicated for 20 min and stirred overnight. After filtration of the latter, 1.2 g (93% yield) of the desired compound as a grey solid was obtained.

$^1$H-NMR (300 MHz, DMSO-d$_6$) δ: 9.58 (bs, 1H); 7.69 (d, J=8.2 Hz, 2H); 7.59 (d, J=8.2 Hz, 2H); 7.54 (d, J=15.6 Hz, 1H); 7.36 (s, 1H); 7.34 (m, 1H); 6.85 (d, J=8.8 Hz, 1H); 6.48 (d, J=16.0 Hz, 1H); 2.11 (bs, 6H); 2.03 (bs, 3H); 1.72 (bs, 6H); 1.47 (s, 9H).

Example 1

(S)-2-amino-3-methyl-butyric acid 3-adamantan-1-yl-4'-((E)-2-carboxy-vinyl)-biphenyl-4-yl ester hydrochloride ST5576CL1

STEP 1: To a solution of BOC-Val-OH (24 mg, 0.11 mmol) in DMF (1 ml) were added PyBOP (57 mg, 0.11 mmol), DIPEA (65 ml, 0.5 mmol) and the reaction mixture, monitored by TLC, was stirred until complete activation of the acid. (E)-3-(3'-Adamantan-1-yl-4'-hydroxy-biphenyl-4-yl)-acrylic acid tert-butyl ester was then added (43 mg, 0.10 mmol) and the the reaction mixture was stirred for 5 h at 0° C.

After standard work-up, the crude product was purified by flash column chromatography (hexane/EtOAc=9/1) to get the desired product in 45% yield.

STEP 2: The latter was dissolved at RT in a DCM/TFA (8/2) mixture and stirred until complete cleavage of the tert-butyl ester moiety. The reaction mixture was then concentrated under reduced pressure and diluted with DCM. The latter procedure was repeated twice to get the crude desired product. The latter was then dissolved in DMSO and then freeze-dried to obtain the desired compound in 83% yield.

$^1$H-NMR (300 MHz, DMSO-d$_6$) δ: 12.40 (bs, 1H); 8.99 (bs, 2H); 7.76 (d, J=8.5 Hz, 2H); 7.70 (d, J=8.5 Hz, 2H); 7.614 (m, 3H); 7.25 (d, J=8.5 Hz, 1H); 6.57 (d, J=15.9 Hz, 1H); 4.2 (d, J=3.1 Hz, 1H); 2.53 (m, 10H); 2.05 (s, 5H); 1.97 (m, 1 H); 1.15 (d, J=7.0 Hz, 3H); 1.12 (d, J=7.0 Hz, 3H). ESI-MS: m/z=474.2 [M+H]$^+$.

Example 2

(E)-3-(3'-adamantan-1-yl-4'-{2-[2-(2-carboxymethoxy-ethoxy)-ethoxy]-acetoxy}-biphenyl-4-yl)-acrylic acid ST5587AA1

STEP 1: It was conducted following the procedure described in example 1 step 1, starting from 3,6,9-trioxaundecanedioic acid and a reaction time of 2.5 h. The desired intermediate t-Bu ester was obtained in 72% yield.

STEP 2: It was conducted following the procedure described in example 1 step 2 without freeze-drying. The desired product was obtained as a solid in 98% yield.

$^1$H-NMR (300 MHz, DMSO-d$_6$) δ: 12.40 (bs, 1H); 7.76 (d, J=8.4 Hz, 2H); 7.70 (d, J=8.4 Hz, 2H); 7.62 (d, J=16 Hz, 1H); 7.56 (m, 2H); 7.18 (d, J=8.71 Hz, 1H); 6.56 (d, J=16 Hz, 1H); 4.49 (s, 2H); 4 (s, 2H); 3.71 (m, 2H); 3.57 (m, 6H); 2.02 (m, 9H); 1.73 (m, 6H).
ESI-MS m/z=601.3 [M+Na]$^+$.

Comparison Example 3 undecanoic acid 3-adamantan-1-yl-4'-((E)-2-carboxy-vinyl)-biphenyl-4-yl ester ST5628AA1

STEP 1: It was conducted following the procedure described in example 1 step 1, starting from undecanoic acid and a reaction time of 13 h. The desired intermediate tert-Bu ester was obtained in 63% yield.

STEP 2: The latter was dissolved at RT in dioxane. HCl (4M, in dioxane) was added at RT and the reaction mixture was stirred until complete conversion of the starting material to the corresponding carboxylic derivative. The reaction mixture was then concentrated under reduced pressure and diluted with DCM. The latter procedure was repeated twice to get the desired product as a white solid (71% yield).

$^1$H-NMR (300 MHz, DMSO-d$_6$) δ: 12.40 (bs, 1H); 7.75 (d, J=8.5 Hz, 2H); 7.68 (d, J=8.5 Hz, 2H); 7.62 (d, J=16.0 Hz, 1H); 7.54 (m, 1H); 7.54 (s, 1H); 7.07 (d, J=9.0 Hz, 1H); 6.55 (d, J=16.0 Hz, 1H); 2.64 (t, J=7.2 Hz, 2H); 2.04 (bs, 3H); 1.99 (bs, 6H); 1.72 (bs, 6H); 1.68 (m, 2H); 1.40-1.20 (bm+bs, 14H); 0.84 (t, J=7.1 Hz).
ESI-MS m/z=543.3 [M+H]$^+$.

Example 4

4-morpholin-4-yl-butyric acid 3-adamantan-1-yl-4'-((E)-2-carboxy-vinyl)-biphenyl-4-yl ester hydrochloride ST5589CL1

STEP 1: 4-bromobutyryl chloride (53 μl, 0.46 mmol) was added dropwise at 0° C. to a solution of (E)-3-(3'-adamantan- 1-yl-4'-hydroxy-biphenyl-4-yl)-acrylic acid tert-butyl ester (100 mg, 0.23 mmol) and DIPEA (80 μl, 0.46 mmol) in DCM (4 ml). The reaction mixture was stirred for 1 h at RT. The reaction mixture was diluted with DCM and washed with $H_2O$. The organic phase was dried over $Na_2SO_4$ and the solvent was removed under reduced pressure. The crude material thus obtained was used in the next step without any further purification.

STEP 2: Morpholine (140 μl, 1.61 mmol) was added to a suspension of the latter bromo derivative in DMF (3 ml) and the reaction mixture was stirred at 50° C. for 12 h. Solvents were removed under reduced pressure, and the residue was purified by flash chromatography (Hexane/EtOAc=⅔) to get the expected product in 54% yield.

STEP 3: It was conducted following the procedure described in example 3 step 2, and gave the desired compound as a solid in 99% yield.

$^1$H-NMR (300 MHz, DMSO-$d_6$) μ: 12.40 (bs, 1H); 7.76 (d, J=7.7 Hz, 2H); 7.70 (d, J=7.7 Hz, 2H); 7.65 (d, J=15.7 Hz, 1H); 7.56 (m, 2H); 7.15 (d, J=9.06 Hz, 1H); 6.56 (d, J=15.7 Hz, 1H); 3.94 (bd, 2H); 3.75 (bt, 2H); 3.44 (bm, 2H); 3.18-3.04 (bm, 6H); 2.80 (t, 2H); 2.03 (m, 9H); 1.74 (bs, 6H).
ESI-MS m/z=530.3 [M+H]$^+$.

Example 5

4-(4-methyl-piperazin-1-yl)-butyric acid 3-adamantan-1-yl-4'-((E)-2-carboxy-vinyl)-biphenyl-4-yl ester dihydrochloride ST5592CL1

STEP 1: It was conducted following the procedure described in example 4 step 2, starting from the product obtained in example 4 step 1 and N-methyl piperazine. The resulting intermediate was purified by flash chromatography (DCM/MeOH=9/1) to allow the obtention of the desired derivative in 26% yield.

STEP 2: It was conducted following the procedure described in example 4 step 3, and gave the desired compound as a solid in 99% yield.

$^1$H-NMR (300 MHz, DMSO-$d_6$) δ: 12.40 (bs, 1H); 7.76 (d, J=8.5 Hz, 2H); 7.69 (d, J=8.5 Hz, 2H); 7.62 (d, J=15.8 Hz, 1H); 7.56 (m, 2H); 7.10 (d, J=8.8 Hz, 1H); 6.56 (d, J=15.8 Hz, 1H); 2.8-3 (bm, 4H); 2.6-2.8 (bm, 6H); 2.4 (bm, 2H); 2.1 (s, 3H); 2.02 (bs, 9H); 1.9 (bm, 2H); 1.78 (bm, 6H). ESI-MS m/z=543.4 [M+H]$^+$.

Example 6

(E)-3-[3'-adamantan-1-yl-4'-(2-methylamino-ethyl-carbamoyloxy)-biphenyl-4-yl]-acrylic acid ST5588CL1

STEP 1: para-nitrophenylchloroformate (174 mg, 0.58 mmol) was added at 0° C. to a solution of (E)-3-(3'-adamantan-1-yl-4'-hydroxy-biphenyl-4-yl)-acrylic acid tert-butyl ester (104 mg, 0.24 mmol) and DIPEA (252 μl, 1.45 mmol) in DCM (5 ml). Then the reaction mixture was stirred for 2 h at RT. N-Boc-N-methylethylenediamine (87 μl, 0.49 mmol) was then added and the reaction mixture was stirred at 55° C. for 14 h. The reaction mixture was diluted with DCM and washed with $H_2O$. The organic phase was dried over $Na_2SO_4$ and the solvent was removed under reduced pressure. The resulting residue was purified by flash chromatography (hexane/EtOAc=8/2) to get the desired intermediate in 65% yield.

STEP 2: It was conducted following the procedure described in example 3 step 2, and gave the desired compound as a white solid in 94% yield.

$^1$H-NMR (300 MHz, DMSO-$d_6$) δ: 12.40 (bs, 1H); 8.90 (bs, 1H); 8.11 (t, J=5.7 Hz 1H); 7.75 (d, J=8.3 Hz, 2H); 7.68 (d, J=8.3 Hz, 2H); 7.62 (d, J=16.0 Hz, 1H); 7.53 (dd, J1=8.1 Hz, J2=1.9 Hz, 1H); 7.51 (s, 1H); 7.17 (d, J=8.1 Hz, 1H); 6.55 (d, J=16.0 Hz, 1H); 3.42 (q, J=6.1 Hz, 2H); 3.03 (t, J=6.4 Hz, 2H); 2.59 (s, 3H); 2.02 (bs, 9H); 1.74 (bt, 6H).
ESI-MS m/z=475.1 [M+H]$^+$.

Example 7

(E)-3-(3'-adamantan-1-yl-4'-carboxymethylcarbamoyloxy-biphenyl-4-yl)-acrylic acid ST5602AA1

STEP 1: It was conducted following the procedure described in example 6 step 1, using Gly-O-tBu instead of N-Boc-N-methylethylenediamine. After addition of the amine the reaction mixture was stirred for 12 h to get the desired intermediate in 61% yield.

STEP 2: It was conducted following the procedure described in example 3 step 2, and gave the desired compound as a white solid in 62% yield.

$^1$H-NMR (300 MHz, DMSO-$d_6$) δ: 12.50 (bs, 1H); 8.15 (t, J=6.1 Hz 1H); 7.75 (d, J=8.5 Hz, 2H); 7.68 (d, J=8.5 Hz, 2H); 7.62 (d, J=16.1 Hz, 1H); 7.54 (m, 1H); 7.50 (s, 1H); 7.02 (d, J=8.4 Hz, 1H); 6.54 (d, J=16.1 Hz, 1H); 3.76 (bd, J=5.0 Hz, 2H); 2.04 (bs, 9H); 1.74 (bm, 6H).
ESI-MS: m/z=476.0 [M+H]$^+$.

Example 8

(E)-3-[3'-adamantan-1-yl-4'-(4-amino-butylcarbamoyloxy)-biphenyl-4-yl]-acrylic acid hydrochloride ST5604CL1

STEP 1: It was conducted following the procedure described in example 6 step 1, using N-Boc-1,4-diaminobutane instead of N-Boc-N-methylethylenediamine. After addition of the amine the reaction mixture was stirred for 12 h to get the desired intermediate in 60% yield.

STEP 2: It was conducted following the procedure described in example 3—step 2, and gave of the desired compound as a solid in 54% yield.

$^1$H-NMR (300 MHz, DMSO-$d_6$) δ: 12.40 (bs, 1H); 7.4-8 (bm, 8H); 7.05 (d, 1H); 6.55 (d, 1H); 3.1 (bm, 2H); 2.8 (bm, 2H); 2.02 (bs, 9H); 1.6-1.8 (bs, 6H); 1.4-1.6 (bs, 4H).
EI-MS m/z=489.4 [M+H]$^+$.

Example 9

(E)-3-[3'-adamantan-1-yl-4'-(2-morpholin-4-yl-ethyl-carbamoyloxy)-biphenyl-4-yl]-acrylic acid hydrochloride ST5606CL1

STEP 1: It was conducted following the procedure described in example 6 step 1, using 4-(2-aminoethyl)-morpholine instead of N-Boc-N-methylethylenediamine. After addition of the amine the reaction mixture was stirred for 12 h to get the desired intermediate in 56% yield.

STEP 2: It was conducted following the procedure described in example 3 step 2, and gave the desired compound as solid in 56% yield.

$^1$H-NMR (300 MHz, DMSO-$d_6$) δ: 12.40 (bs, 1H); 8.2 (bt, 1H); 7.75 (d, J=8 Hz, 2H); 7.68 (d, J=8 Hz, 2H); 7.61 (d, J=16.1 Hz, 1H); 7.53 (m, 2H); 7.15 (d, J=7.86 Hz, 1H); 6.55 (d, J=16.1 Hz, 1H); 3.95 (bm, 2H); 3.81 (t, 2H); 3.53 (m, 4H); 3.1-3.3 (m, 4H); 2.02 (bs, 9H); 1.74 (bm, 6H).
ESI-MS m/z=531.4 [M+H]$^+$.

Example 10

(E)-3-(3'-adamantan-1-yl-4'-undecyl-carbamoyloxy-biphenyl-4-yl)-acrylic acid ST5629AA1

STEP 1: It was conducted following the procedure described in example 6 step 1, using undecylamine instead of N-Boc-N-methylethylenediamine. After addition of the amine the reaction mixture was stirred for 12 h to get the desired intermediate in 83% yield.

STEP 2: It was conducted following the procedure described in Example 3, Step 2, allowing the obtention of the desired compound as a white powder in 80% yield.

$^1$H-NMR (300 MHz, DMSO-$d_6$) δ: 12.40 (bs, 1H); 7.82 (t, J=5.8 Hz 1H); 7.75 (d, J=8.5 Hz, 2H); 7.67 (d, J=8.5 Hz, 2H); 7.61 (d, J=15.8 Hz, 1H); 7.50 (m, 1H); 7.49 (s, 1H); 7.01 (d, J=8.9 Hz, 1H); 6.54 (d, J=15.8 Hz, 1H); 3.08 (q, J=6.4 Hz, 2H); 2.02 (bs, 9H); 1.74 (bt, 6H); 1.44 (m, 2H); 1.40-1.23 (bm, 16H); 0.83 (t, J=6.9 Hz, 3H).

ESI-MS m/z=572.5 [M+H]$^+$.

Example 11

[1,4']bipiperidinyl-1'-carboxylic acid 3-adamantan-1-yl-4'-((E)-2-carboxy-vinyl)-biphenyl-4-yl ester hydrochloride ST5630CL1

STEP 1: It was conducted following the procedure described in example 6 step 1, using 4-piperidinopiperidine instead of N-Boc-N-methylethylenediamine. After addition of the amine the reaction mixture was stirred for 12 h to get the desired intermediate in 46% yield.

STEP 2: It was conducted following the procedure described in Example 3, Step 2, allowing the obtention of the desired compound as a white powder in 61% yield.

$^1$H-NMR (300 MHz, DMSO-$d_6$) δ: 12.40 (bs, 1H); 10.57 (bs, 1H); 7.77 (d, J=8.4 Hz, 2H); 7.71 (d, J=8.4 Hz, 2H); 7.64 (d, J=15.9 Hz, 1H); 7.55 (m, 2H); 7.10 (d, J=9.0 Hz, 1H); 6.58 (d, J=15.9 Hz, 1H); 4.29 (m, 2H); 3.39 (m, 2H); 2.94 (m, 4H); 2.24 (m, 2H); 2.05 (m, 9H); 1.81 (m, 14H).

ESI-MS m/z=569.4 [M+H]$^+$.

Example 12

(E)-3-(3'-adamantan-1-yl-4'-isopropylcarbamoyloxy-biphenyl-4-yl-acrylic acid ST5536AA1

Isopropyl isocyanate (327 μl, 3.33 mmol) was added at RT to a solution of (E)-3-(3'-adamantan-1-yl-4'-hydroxy-biphenyl-4-yl)-acrylic acid (200 mg, 0.53 mmol), NEt$_3$ (314 μl, 2.44 mmol) and the reaction mixture was stirred for 5 days. The reaction mixture was diluted with DCM and washed with H$_2$O. The organic phase was dried over Na$_2$SO$_4$ and the solvent was removed under reduced pressure.

The desired compound was obtained without any further purification as a solid in 68% yield.

$^1$H-NMR (300 MHz, DMSO-$d_6$) δ: 12.40 (bs, 1H); 7.7 (bd, H); 7.74 (d, J=8.2 Hz, 2H); 7.67 (d, J=8.2 Hz, 2H); 7.60 (d, J=15.9 Hz, 1H); 7.51 (m, 2H); 7.04 (d, J=8.9 Hz, 1H); 6.58 (d, J=15.9 Hz, 1H); 3.70 (m, 1H); 2.02 (bs, 9H); 1.74 (m, 6H); 1.14 (s, 3H); 1.12 (s, 3H).

ESI-MS m/z=458.1 [M−H]$^-$.

Example 13

4-[3-adamantan-1-yl-4'-((E)-2-carboxy-vinyl)-biphenyl-4-yloxycarbonylamino]-piperidine-1-carboxylic acid benzyl ester ST5577AA1

STEP 1: It was conducted following the procedure described in example 12, using benzyl 4-isocyanatotetrahydro-1(2H)-pyridine carboxylate instead of isopropyl isocyanate. The reaction mixture was stirred for 2 days to yield 37% of the desired product.

STEP 2: It was conducted following the procedure described in example 2 step 2. The desired product was obtained as a solid in 69% yield.

$^1$H-NMR (300 MHz, DMSO-$d_6$) δ: 12.40 (bs, 1H); 7.92 (d, 1H); 7.74 (d, J=8.2 Hz, 2H); 7.68 (d, J=8.2 Hz, 2H); 7.61 (d, J=15.9 Hz, 1H); 7.5 (m, 2H); 7.32-7.42 (m, 5H); 7.03 (d, J=8.9 Hz, 1H); 6.54 (d, J=15.9 Hz, 1H); 5.07 (s, 2H); 3.95 (dd, 2H); 3.6 (m, 1H); 2.9-3.1 (bm, 2H); 2.02 (bs, 9H); 1.9-1.8 (dd, 2H); 1.73 (m, 6H); 1.42 (m, 2H).

ESI-MS m/z=633.3 [M−H].

Example 14

(E)-3-{3'-Adamantan-1-yl-4'-[(S)-1-(carboxymethyl-carbamoyl)-3-methyl-butylcarbamoyloxy]-biphenyl-4-yl}-acrylic acid ST5690AA1

STEP 1: It was conducted following the procedure described in example 6 step 1, using tert-BuOGlyLeuNH$_2$ instead of N-Boc-N-methylethylenediamine. After addition of the amine the reaction mixture was stirred for 16 h at RT to get the desired intermediate in 71% yield after purification by silica gel chromatography with a gradient hexane/EtOAc 4:1 to 3:1.

STEP 2: It was conducted following the procedure described in example 3 step 2, and gave the desired compound as an oil in 40% yield.

ESI-MS m/z=587.6 [M−H]$^-$.

Example 15

(E)-3-[3'-Adamantan-1-yl-4'-(2-methoxy-ethoxymethoxy)-biphenyl-4-yl]acrylic acid ST5583AA1

STEP 1: A solution of (E)-3-(3'-adamantan-1-yl-4'-hydroxybiphenyl-4-yl)-acrylic acid methyl ester (120 mg, 0.309 mmol) in 1 ml of anhydrous DMF, was dropped into a 1 ml suspension of NaH (14.8 mg, 0.371 mmol, 60% in mineral oil) in anhydrous DMF (0.3 ml) at 0° C. The resulting red solution was stirred at RT for 30 min, then MEM-Cl (46 mg, 0.371 mmol) was added. After stirring overnight at RT, iced water was added and the mixture was extracted several times with EtOAc. The combined organic phases were dried over Na$_2$SO$_4$, filtered and concentrated under vacuo. The resulting crude product was purified on silica gel (acetone:hexane 15:85) to obtain (E)-3-[3'-adamantan-1-yl-4'-(2-methoxy-ethoxymethoxy)-biphenyl-4-yl]-acrylic acid methyl ester (123 mg, 84%).

$^1$H-NMR (300 MHz, acetone-$d_6$) δ: 7.80 (m, 5H); 7.48-7.55 (m, 2H); 7.25 (d, J=8.5 Hz, 1H); 6.60 (d, J=8.8 Hz, 1H); 5.42 (s, 2H); 3.85-3.95 (m, 2H) 3.75 (s, 3H); 3.55-3.65 (m, 2H); 3.30 (s, 3H); 2.10 (s, 6H); 2.05 (s, 3H); 1.80 (s, 6H).

STEP 2: The above obtained (E)-3-[3'-adamantan-1-yl-4'-(2-methoxyethoxymethoxy)-biphenyl-4-yl]-acrylic acid methyl ester (56 mg, 0.117 mmol) was added to a solution of LiOH.H$_2$O (24 mg, 0.585 mmol) in 4.8 ml of a mixture THF:H$_2$O 1:1. The resulting solution was stirred at RT overnight. THF was removed under vacuo, and the resulting aqueous solution was acidified with 1N HCl to allow a white precipitate to form. The title compound was obtained after filtration (55 mg, 100%).

$^1$H-NMR (300 MHz, DMSO-d$_6$) δ: 7.60-7.80 (m, 4H); 7.52 (d, J=16 Hz, 1H); 7.45 (d, J=8.1 Hz, 1H); 7.40 (s, 1H); 7.15 (d, J=8.1 Hz, 1H); 6.55 (d, J=16 Hz, 1H); 5.35 (s, 2H); 3.70-3.80 (m, 2H); 3.40-3.50 (m, 2H); 3.20 (s, 3H); 2.12 (s, 6H); 2.04 (s, 3H); 1.75 (s, 6H).

Example 16

(E)-cyclopropanecarboxylic acid 3-adamantan-1-yl-4'-(2-carboxyvinyl)-biphenyl-4-yl ester ST5610AA1

STEP 1: To a suspension of 3-(3'-adamantan-1-yl-4'-hydroxy-biphenyl-4-yl)-acrylic acid (200 mg, 0.534 mmol) in DMF (3 ml), morpholine (60 mg, 0.694 mmol) and TBDPSiCl (166 mg, 0.587 mmol) were added. The resulting mixture was stirred at RT for 20 min and then diluted with DCM. The organic solution was washed several times with water, dried over Na$_2$SO$_4$, filtered and concentrated in vacuo. The resulting product was purified on silica gel (ethyl acetate:hexane 15:85) to obtain (E)-3-(3'-adamantan-1-yl-4'-hydroxybiphenyl-4-yl)acrylic acid tert-butyldiphenylsilyl ester (237 mg, 72%).

$^1$H NMR (DMSO-d$_6$) δ: 9.6 (s, 1H); 7.60-7.85 (m, 10H); 7.35-7.55 (m, 8H); 6.89 (d, J=8.6 Hz, 1H); 6.78 (d, J=16 Hz, 1H); 2.13 (s, 6H); 2.04 (s, 3H); 1.75 (s, 6H); 1.1 (s, 9H).

STEP 2: Cyclopropanecarbonyl chloride (33 mg, 0.318 mmol) was added to a solution of the above obtained derivative (130 mg, 0.212 mmol) in pyridine (1 ml). The resulting solution was heated to 50° C. for 30 min, then diluted with water and extracted with EtOAc. The organic layer was washed with 1N HCl, dried over Na$_2$SO$_4$, filtered and concentrated under vacuo. The desired cyclopropanecarboxylic acid (E)-3-adamantan-1-yl-4'-(2-tert-butyldiphenylsilyloxyvinyl) biphenyl-4-yl ester was obtained after purification on silica gel (EtOAc: hexane 90:10) in 42% yield (61 mg).

$^1$H NMR (CDCl$_3$) δ: 7.70-7.80 (m, 6H); 7.50-7.70 (m, 5H); 7.30-7.50 (m, 7H); 7.08 (d, J=8.6 Hz, 1H); 6.56 (d, J=16 Hz, 1H); 2.15 (s, 9H); 1.91-1.96 (m, 1H); 1.76 (s, 6H); 1.20-1.26 (m, 2H); 1.15 (s, 9H); 1.00-1.08 (m, 2H).

STEP 3: TBAF (1N THF solution, 221 μl) was added at −78° C. to a solution of cyclopropanecarboxylic acid (E)-3-adamantan-1-yl-4'-(2-tert-butyldiphenylsilyloxyvinyl)-biphenyl-4-yl ester (30 mg, 0.0441 mmol) in THF (2 mL). The mixture was stirred at −78° C. for 30 min and a NH$_4$Cl saturated solution was added. The THF was removed under vacuo and the residue was taken up with water. The solid precipitate was filtered and washed with Et$_2$O, to obtain cyclopropanecarboxylic acid (E)-3-adamantan-1-yl-4'-(2-carboxyvinyl)biphenyl-4-yl ester (12 mg, 62%).

$^1$H NMR (DMSO-d$_6$) δ: 7.70-7.82 (m, 4H); 7.65 (d, J=16 Hz, 1H); 7.50-7.60 (m, 2H); 7.10 (d, J=8.6 Hz, 1H); 6.56 (d, J=16 Hz, 1H); 1.95-2.10 (m, 10H); 1.76 (s, 6H); 1.00-1.15 (m, 4H).

Example 17

(E)-3-[3'-Adamantan-1-yl-4'-(1,3-dioxo-1,3-dihydroisoindol-2-ylmethoxy)-biphenyl-4yl]-acrylic acid ST5632AA1

STEP 1: A solution of (E)-3-(3'-adamantan-1-yl-4'-hydroxybiphenyl-4-yl)acrylic acid tert-butyl ester (200 mg, 0.464 mmol), N-chloromethylphthalimide (91 mg, 0.464 mmol), K$_2$CO$_3$ (70 mg, 0.464 mmol) and NaI (70 mg, 0.464 mmol) was stirred overnight at RT in the dark. The solvent was evaporated and the residue was taken up in EtOAc. The organic phase was washed with water, dried over Na$_2$SO$_4$, filtered and evaporated under reduced pressure. 3-[3'-Adamantan-1-yl-4'-(1,3-dioxo-1,3-dihydroisoindol-2-ylmethoxy)-biphenyl-4-yl]acrylic acid tert-butyl ester was obtained after purification on silica gel (EtOAc/hexane 15:85) in 55% yield (150 mg).

$^1$H NMR (DMSO-d$_6$) δ: 7.30-8.05 (m, 12H); 6.55 (d, J=16 Hz, 1H); 5.70 (s, 2H); 2.05 (s, 6H); 1.95 (s, 3H); 1.60 (s, 6H); 1.50 (s, 9H).

STEP 2: TFA (1.8 ml) was dropped into an ice-cooled solution of (E)-3-[3'-adamantan-1-yl-4'-(1,3-dioxo-1,3-dihydroisoindol-2-ylmethoxy)-biphenyl-4-yl]acrylic acid tert-butyl ester (110 mg, 0.186 mmol) in DCM (1.8 ml), and the mixture was stirred at 0° C. for 10 min. The solvent was removed in vacuo and the residue was rinsed with hexane to obtain, after filtration, 97 mg (98%) of the title compound.

$^1$H NMR (DMSO-d$_6$) δ: 7.30-8.10 (m, 12H); 6.58 (d, J=16 Hz, 1H); 5.69 (s, 2H); 2.05 (s, 6H); 1.95 (s, 3H); 1.60 (s, 6H).

Example 18

(E)-Octadeca-9,12-dienoic acid 3-adamantan-1-yl-4'-(2-carboxyvinyl)-biphenyl-4-yl ester ST5633AA1

STEP 1: Linoleoyl chloride (208 mg, 0.696 mmol) was added to a solution of (E)-3-(3'-adamantan-1-yl-4'-hydroxybiphenyl-4-yl)-acrylic acid tert-butyl ester (200 mg, 0.464 mmol) in pyridine (2.2 ml). The resulting mixture was heated to 50° C. for 1 h, and then stirred at RT overnight. After addition of EtOAc, the organic phase was washed twice with 1N HCl, water, dried over Na$_2$SO$_4$, filtered and removed under reduced pressure. (E)-Octadeca-9,12-dienoic acid 3-adamantan-1-yl-4'-(2-tert-butoxycarbonylvinyl)biphenyl-4-yl ester was obtained as a colourless oil after purification on silica gel (EtOAc/hexane 5:95) in 65% yield (210 mg).

$^1$H NMR (DMSO-d$_6$) δ: 7.50-7.80 (m, 7H); 7.10 (d, J=8.5, 1H); 6.58 (d, J=16 Hz, 1H); 5.25-5.45 (m, 4H); 2.60-2.80 (m, 4H); 1.9-2.10 (m, 11H); 1.71 (s, 6H); 1.50 (s, 9H); 1.20-1.40 (m, 16H); 0.8-0.9 (m, 3H).

STEP 2: TFA (1.6 ml) was dropped into an ice-cooled solution of octadeca-9,12-dienoic acid (E)-3-adamantan-1-yl-4'-(2-tert-butoxycarbonylvinyl)biphenyl-4-yl ester (110 mg, 0.159 mmol) in DCM (1.6 ml) and the resulting solution was stirred for 30 min at 0° C. The solvent was removed under reduced pressure to obtain the title compound as a white solid (100 mg, 99%).

$^1$H NMR (DMSO-d$_6$) δ: 7.55-7.85 (m, 7H); 7.10 (d, J=8.5 Hz, 1H); 6.59 (d, J=16 Hz, 1H); 5.20-5.40 (m, 4H); 2.60-2.80 (m, 4H); 1.9-2.10 (m, 11H); 1.71 (s, 6H); 1.15-1.45 (m, 16H); 0.8-0.9 (m, 3H).

Example 19

(E)-3-(3'-Adamantan-1-yl-4'-propoxycarbonyloxymethoxy-biphenyl-4-yl-acrylic acid ST5688AA1

STEP 1: A mixture of (E)-3-(3'-adamantan-1yl-4'-hydroxybiphenyl-4-yl)acrylic acid tert-butyl ester (250 mg, 0.581 mmol) and K$_2$CO$_3$ (241 mg, 1.74 mmol) in water (2.9 ml) was stirred at RT for 30 min. Tetrabutylammonium hydrogen sulfate (197 mg, 0.581 mmol) and DCM (1.4 ml) were then added and the stirring maintained for further 10 min. A solution of carbonic acid iodomethyl ester propyl ester (184 mg, 0.755 mmol) in DCM (1.4 ml) was then added dropwise. The biphasic solution was stirred overnight at RT. After standard work-up and removal of the solvent under reduced pressure, the residue was taken up in Et$_2$O. Tetrabutylammonium iodide was filtered off and the solvent was evaporated. (E)-3-(3'-Adamantan-1-yl-4'-propoxycarbonyloxymethoxy-biphenyl-4-yl)acrylic acid tert-butyl ester was obtained (117 mg, 36%) after purification on silica gel (EtOAc/hexane 12:88).

$^1$H NMR (acetone-d$_6$) δ: 7.55-7.80 (m, 7H); 7.25 (d, J=8.6 Hz, 1H); 6.51 (d, J=16 Hz, 1H); 6.00 (s, 2H); 4.11-4.20 (m, 2H); 2.05-2.20 (m, 9H); 1.85 (s, 6H); 1.60-1.75 (m, 2H); 1.51 (s, 9H); 0.90-1.00 (m, 3H).

STEP 2: A mixture of (E)-3-(3'-adamantan-1-yl-4'-propoxycarbonyloxymethoxy-biphenyl-4-yl)-acrylic acid tert-butyl ester (40 mg, 0.073 mmol) and montmorillonite KSF (15 mg) was refluxed in MeCN (1 ml) for 2 h. The reaction mixture was diluted by means of EtOAc, and filtered. The solvent was removed under reduced pressure. The title compound (10 mg, 28%) was obtained after purification on silica gel (EtOAc/hexane 60:40).

$^1$H NMR (acetone-d$_6$) δ: 7.55-7.85 (m, 7H); 7.30 (d, J=8.6 Hz, 1H); 6.60 (d, J=16 Hz, 1H); 6.00 (s, 2H); 4.10-4.20 (m, 2H); 2.00-2.20 (m, 9H); 1.85 (s, 6H); 1.65-1.75 (m, 2H); 0.90-1.00 (m, 3H).

Example 20

(E)-1-[3-Adamantan-1-yl-4'-(2-carboxyvinyl)-biphenyl-4-yloxycarbonyl]-cyclopropyl-ammonium trifluoroacetate ST5667TF1

STEP 1: PyBop (388 mg, 0.745 mmol), 1-(Boc-amino)cyclopropanecarboxylic acid (150 mg, 0.745 mmol) and DIPEA (438 mg, 3.39 mmol) were added to a solution of (E)-3-(3'-adamantan-1-yl-4'-hydroxybiphenyl-4-yl)-acrylic acid tert-butyl ester (291 mg, 0.677 mmol) in DMF (3.4 ml). The mixture was stirred at RT for 6 h, and then diluted with EtOAc. The solution was washed with 1N HCl, dried over Na$_2$SO$_4$ and filtered. Solvent was removed under reduced pressure. The crude reaction mixture was purified on silica gel (EtOAc/hexane 15:85) and then crystallized from Et$_2$O to afford (E)-1-tert-butoxycarbonylaminocyclopropanecarboxylic acid 3-adamantan-1-yl-4'-(2-tert-butoxycarbonylvinyl)-biphenyl-4-yl ester (160 mg, 38%).

$^1$H NMR (DMSO-d$_6$) δ: 7.55-7.82 (m, 7H); 6.95 (d, J=8.6 Hz, 1H); 6.58 (d, J=16 Hz, 1H); 2.00-2.10 (m, 9H); 1.65-1.85 (m, 6H); 1.40-1.60 (m, 2H); 1.50 (s, 9H); 1.35 (s, 9H); 1.20-1.30 (m, 2H).

STEP 2: It was conducted following the procedure described in example 18 step 2. The desired product was obtained in quantitative yield.

$^1$H NMR (DMSO-d$_6$) δ: 9.00 (bs, 3H); 7.55-7.85 (m, 7H); 7.10 (d, 1Ar, J=8.6 Hz, 1H); 6.60 (d, J=16 Hz, 1H); 2.10 (s, 3H); 1.98 (s, 6H); 1.70-1.85 (m, 8H); 1.55-1.65 (m, 2H).

Example 21

(E)-3-(3'-Adamantan-1-yl-4'-cyanomethoxybiphenyl-4-yl)-acrylic acid ST5741AA1

STEP 1: Bromoacetonitrile (84 mg, 0.7 mmol), K$_2$CO$_3$ (166 mg, 1.2 mmol) and KI (53 mg, 0.32 mmol) were added to a solution of (E)-3-(3'-adamantan-1-yl-4'-hydroxybiphenyl-4-yl)-acrylic acid methyl ester (250 mg, 0.64 mmol) in DMF (2 ml). The mixture was stirred at RT for 3 h. Cold water was added and the solution was extracted with EtOAc. The organic layer was washed with a saturated solution of NaHCO$_3$, water and brine. The organic layer was dried over Na$_2$SO$_4$ and evaporated under reduced pressure to obtain (E)-3-(3'-adamantan-1-yl-4'-cyanomethoxybiphenyl-4-yl)-acrylic acid methyl ester (240 mg, 88%).

$^1$H NMR (DMSO-d$_6$) δ: 7.42-7.88 (m, 7H); 7.20 (d, J=8.5 Hz, 1H); 6.78 (d, J=16 Hz, 1H); 5.28 (s, 2H); 3.71 (s, 3H); 2.10 (s, 9H); 1.75 (s, 6H).

STEP 2: (E)-3-(3'-Adamantan-1-yl-4'-cyanomethoxybiphenyl-4-yl)-acrylic acid methyl ester (240 mg, 0.56 mmol) was added to a solution of LiOH.H$_2$O (117 mg, 2.8 mmol) in 24 ml of THF:H$_2$O 1:1. The solution thus obtained was kept under stirring at RT overnight. THF was removed under reduced pressure and the resulting aqueous layer acidified with 1N HCl to allow the formation of the title compound as a white precipitate that was filtered (216 mg, 93%).

$^1$H NMR (DMSO-d$_6$) δ: 7.44-7.78 (m, 7H); 6.98 (d, J=8.6 Hz, 1H); 6.51 (d, J=16 Hz, 1H); 4.50 (s, 2H); 1.98-2.10 (m, 9H); 1.71 (s, 6H).

Example 22

(E)-3-(3'-Adamantan-1-yl-4'-amidemethoxybiphenyl-4-yl)-acrylic acid ST5765AA1

This compound was obtained according to the procedure described in example 21, Step 2 and effecting the acidification with 1N HCl at 50° C. for 6 h.

$^1$H NMR (DMSO-d$_6$) δ: 1.71 (s, 6H); 1.98-2.10 (m, 9H); 5.28 (s, 2H); 6.55 (d, 1H, J=16 Hz); 7.20 (d, 1H J=8.6 Hz); 7.29 (bs, 2H); 7.44-7.78 (m, 7H).

Example 23

(E)-3-[3'-Adamantan-1-yl-4'-(2-morpholin-4-yl-ethoxy)biphenyl-4-yl]-acrylic acid ST5743CL 1

STEP 1: K$_2$CO$_3$ (265 mg, 1.92 mmol) was added to a solution of (E)-3-(3'-adamantan-1-yl-4'-hydroxybiphenyl-4-yl)-acrylic acid methyl ester (250 mg, 0.64 mmol) in DMF (2.5 ml) and the mixture was stirred at RT for 30 min. 4-(2-Chloroethyl)-morpholine hydrochloride (155 mg, 0.83 mmol) was added and the solution was heated to 60° C. for 14 h. The reaction was quenched by addition of water and was extracted with EtOAc. The organic layer was washed with a saturated solution of NaHCO$_3$, water and brine, dried over Na$_2$SO$_4$ and evaporated under reduced pressure to obtain (E)-3-[3'-adamantan-1-yl-4'-(2-morpholin-4-yl-ethoxy)biphenyl-4-yl]-acrylic acid methyl ester (193 mg, 60%) after purification on silica gel (EtOAc:hexane 50:50).

$^1$H NMR (DMSO-d$_6$) δ: 7.75 (d, J=16 Hz, 1H); 7.30-7.65 (m, 6H); 6.90 (d, J=8.5 Hz, 1H); 6.45 (d, J=16 Hz, 1H); 4.10-4.25 (m, 2H); 3.80 (s, 3H); 3.60-3.75 (m, 4H); 2.80-2.90 (m, 2H); 2.50-2.70 (m, 4H); 2.20 (s, 6H); 2.05 (s, 3H); 1.70 (s, 6H).

Example 24

(E)-Methanesulfonic acid 3-adamantan-1-yl-4'-(2-carboxyvinyl)-biphenyl-4-yl ester ST7259AA1

Methanesulfonyl chloride (91.8 mg, 0.802 mmol) and triethylamine (162 mg, 1.60 mmol) were added to a solution of (E)-3-(3'-adamantan-1-yl-4'-hydroxy-biphenyl-4-yl)-acrylic acid (150 mg, 0.401 mmol) in THF (1.60 ml) at 0° C. and the resulting mixture was stirred for 1 h. The latter was diluted with EtOAc, washed with 1N HCl and dried over $Na_2SO_4$ and concentrated in vacuo. The residue was purified by crystallization from EtOAc/isopropyl ether 1:1 to afford 20 mg (11%) of product as a white powder.

$^1$H NMR (DMSO-$d_6$) δ: 7.83-7.69 (m, 4H), 7.65 (dd, J=7.96 Hz, J=2.32 Hz, 1H), 7.61 (1H, s), 7.58 (d, J=16.03 Hz, 1H), 7.54 (d, J=7.96 Hz, 1H), 6.58 (d, J=16.03 Hz, 1H), 3.61 (s, 3H), 2.09 (s, 9H), 1.75 (s, 6H).

Example 25

Chemical Stability

The compounds were screened at various pH in order to test their relative chemical stability in solution. All of them resulted stable after incubation for 3 h at pH=1.2. Chemical stability was also investigated at pH=7.4 after 24 h incubation. The results are reported in Table 1.

TABLE 1

| Examples | % Recovery after 24 h at pH 7.4 |
| --- | --- |
| 1 | 12 |
| 2 | Stable |
| 3 | Stable |
| 4 | 88 |
| 5 | 64 |
| 6 | 37 |
| 7 | Stable |
| 8 | Stable |
| 9 | 90 |
| 10 | Stable |
| 11 | Stable |
| 12 | Stable |
| 13 | Stable |
| 14 | NT |
| 15 | Stable |
| 16 | Stable |
| 17 | Stable |
| 18 | NT |
| 19 | Stable |
| 20 | 62 |
| 21 | NT |
| 23 | NT |

Stable means that recovery > 98%; NT: not tested

It is interesting to note that for all the compounds which showed a stability less than 98%, the amount of E-4-(3-(1-adamantyl)-4-hydroxyphenyl)cinnamic acid was always less than or equal to 3% except for example 20 where the hydrolysed parent compound was found to be present in 8%.

Biological Activities

Cytotoxicity on NCI-H460 Tumor Cell Line

To evaluate the effect of the compounds on survival cells, the sulphorodamine B test was used. To test the effects of the compounds on cell growth, NCI-H460 non-small cell lung carcinoma cells were used. Tumor cells were grown in RPMI 1640 containing 10% fetal bovine serum (GIBCO).

Tumor cells were seeded in 96-well tissue culture plates at approximately 10% confluence and were allowed to attach and recover for at least 24 h. Varying concentrations of the drugs were then added to each well to calculate their $IC_{50}$ value (the concentration which inhibits the 50% of cell survival). The plates were incubated at 37° C. for 24 h. At the end of the treatment, the plates were washed by remotion of the surnatant and addition of PBS. Medium culture (200 μL) was added again and the plates were incubated for further 48 h at 37° C. 200 μl PBS and 50 μl of cold 80% TCA were added. The plates were incubated on ice for at least 1 h. TCA was removed, the plates were washed 3 times for immersion in distilled-water and dried on paper and at 40° C. for 5 min. Then 200 μl of 0.4% sulphorodamine B in 1% acetic acid were added. The plates were incubated at room temperature for other 30 min. Sulphorodamine B was removed, the plates were washed for immersion in 1% acetic acid for 3 times, then they were dried on paper and at 40° C. for 5 min. Then 200 μl Tris 10 mM were added, the plates were kept under stirring for 20 min. The survival cell was determined as optical density by a Multiskan spectrofluorimeter at 540 nm. The amount of cells killed was calculated as the percentage decrease in sulphorodamine B binding compared with control cultures, the latter involving the use of (2E)-3-[3'-(1-adamantyl)-4'-hydroxy[1,1'-biphenyl]-4-yl]-2-propenoic acid (ST1926).

The $IC_{50}$ values were calculated with the "ALLFIT" program.

Results

The compounds of the present invention were evaluated for their antiproliferative effect on NCI-H460 non-small lung carcinoma cells (Table 2). Unexpectedly, a lot of these derivatives exhibited an inhibitory activity comparable or even better than the one of the structurally related analogue ST1926. Moreover, taking into consideration of the chemical stability data reported in Table 1, the activity demonstrated does not result from hydrolysis of the respective groups present on the oxygen atom present in position 4'.

TABLE 2

Antiproliferative effect ($IC_{50}$) on non small cell lung cancer

| Examples | NCI-H460 $IC_{50}$ μM ± SD μM |
| --- | --- |
| 1 | 0.51 ± 0.003 |
| 2 | 0.17 ± 0.007 |
| 3* | 1.54 ± 0.08 |
| 4 | 0.22 ± 0.009 |
| 5 | 0.24 ± 0.01 |
| 6 | 0.24 ± 0.008 |
| 7 | 3.0 ± 0.1 |
| 8 | 2.6 ± 0.08 |
| 9 | 0.92 ± 0.05 |
| 10 | 1.39 ± 0.04 |
| 11 | >20 |
| 12 | 5 |
| 13 | 5 |
| 14 | 3.5 ± 0.2 |
| 15 | 4.2 ± 0.04 |
| 16 | 0.85 ± 0.03 |
| 17 | 8.4 ± 1.6 |
| 18 | 7.8 ± 0.7 |
| 19 | 0.32 ± 0.01 |
| 20 | 0.10 ± 0.003 |
| 21 | 0.85 ± 0.06 |
| 23 | >5 |
| Control | 0.13 |

*comparison example

Cytotoxicity on A2780 Tumor Cell Line

Preliminary results indicate that the present compounds are also potent inhibitors of the proliferation of the human ovarian cancer cell line A2780. The antiproliferative effect of the compounds is reported as percentages of inhibition of cellular proliferation measured at 5 μM as reported in table 3.

TABLE 3

Antiproliferative effect ($IC_{50}$) on ovarian cell cancer

| Examples | % Inhibition at 5 Mm on A2780 cell line |
| --- | --- |
| 1 | 93% |
| 2 | 93% |

TABLE 3-continued

Antiproliferative effect (IC$_{50}$) on ovarian cell cancer

| Examples | % Inhibition at 5 Mm on A2780 cell line |
|---|---|
| 3* | 94% |
| 4 | 94% |
| 5 | 92% |
| 6 | 93% |
| 7 | 26% |
| 8 | 70% |
| 9 | 90% |
| 10 | 90% |
| 13 | 71% |
| 15 | 78% |
| 16 | 93% |
| 18 | 55% |
| 20 | 94% |

*comparison example

In Vivo Study on A431 Epidermoid Carcinoma

The tumour was generated by subcutaneous injection of A431 tumour cells (5×10$^6$/100 μl/mouse), in 0.1 ml medium Tc199 in the right flank of CD1 nude mice. 3 days after tumour injection, ST5589 was delivered iv at a dose of 10 mg/10 ml/kg according to the schedule qdx3/wx2w in a group of 9 mice.

To evaluate the antitumour activity of ST5589, tumour diameters were measured biweekly with a Vernier caliper and tumour volume was calculated according to the formula $$TV = d^2 \times D/2$$

where d and D are the shortest and longest diameters, respectively.

The efficacy of the drug was assessed as the tumour volume inhibition according to the formula reported underneath:

$$TVI\% = 100 - \left[\left(\frac{\text{mean } TV \text{ of treated group}}{\text{mean } TV \text{ of control group}}\right) \times 100\right]$$

After two weeks of treatment, a 34% reduction in tumour volume was found (p=0.036 versus vehicle treated group—Mann-Whitney test) denoting a substantial activity of this derivative.

The invention claimed is:

1. A compound having the general formula I

Formula I

Wherein

R$^1$ is H, O(CO)OR$^4$, NR$^4$R$^5$, CN, alkyl, cycloalkyl or heterocycloalkyl; wherein alkyl, cycloalkyl and heterocycloalkyl are optionally substituted once or more with C$_1$-C$_6$ alkyl, (CH$_2$)$_n$COR$^3$, O(CO)OR$^4$, OH or NR$^4$R$^5$; n is 0 or 1;

R$^3$ is OH, amino, (C$_1$-C$_3$)-alkyl-amino or benzyloxy;

R$^4$ and R$^5$ are the same or different and are each H or alkyl; or

R$^4$ and R$^5$ taken together with the nitrogen atom to which they are attached form a heterocycloalkyl group; or NR$^4$R$^5$ form a nitro group;

R$^2$ is alkylene, hydroxyalkylene, aminocarbonylalkylene, (C$_2$-C$_{18}$)-alkenylene, (C$_3$-C$_6$)-cycloalkylene, heterocycloalkylene, —(OCH$_2$CH$_2$)$_m$—O—, branched or linear polyaminoalkylene, phenyloxy optionally substituted with NO$_2$; or is absent;

m is an integer from 1 to 4;

A is CH$_2$—, —CO—, —CH$_2$—(CO)—, —NH(CO)— or —[CO—(CHR$^6$)—NH]$_w$—;

R$^6$ is the side chain of a natural amino acid radical;

w is 1; or tautomers, geometrical isomers, optically active forms or pharmaceutically acceptable salts thereof;

with the proviso that R$^1$—R$^2$-A does not represent alkyl or alkyl-CO.

2. A compound according to claim 1, wherein independently, A represents —CH$_2$—, —CO—, —[CO—(CHR$^6$)—NH]$_w$—, or —NH(CO)—; R$^1$ represents alkyl, cycloalkyl or heterocycloalkyl and R$^2$ represents alkylene or —(OCH$_2$CH$_2$)$_m$—O—.

3. A compound according to claim 1 wherein R$^1$ represents —O(CO)OR$^4$.

4. A compound according to claim 1 selected from the group consisting of: (S)-2-amino-3-methyl-butyric acid 3-adamantan-1-yl-4'-((E)-2-carboxy-vinyl)-biphenyl-4-yl ester hydrochloride; (E)-3-(3'-adamantan-1-yl-4'-{2-[2-(2-carboxymethoxy-ethoxy)-ethoxy]-acetoxyl}-biphenyl-4-yl)-acrylic acid; 4-morpholin-4-yl-butyric acid 3-adamantan-1-yl-4'-((E)-2-carboxy-vinyl)-biphenyl-4-yl ester hydrochloride; 4-(4-methyl-piperazin-1-yl)-butyric acid 3-adamantan-1-yl-4'-((E)-2-carboxy-vinyl)-biphenyl-4-yl ester dihydrochloride; (E)-3-[3-adamantan-1-yl-4'-(2-methylamino-ethylcarbamoyloxy)-biphenyl-4-yl]-acrylic acid; (E)-3-[3'-adamantan-1-yl-4'-(2-morpholin-4-yl-ethyl-carbamoyloxy)-biphenyl-4-yl]-acrylic acid hydrochloride; cyclopropanecarboxylic acid 3-adamantan-1-yl-4'4(E)-2-carboxy-vinyl)-biphenyl-4-yl ester; (E)-3-(3'-adamantan-1-yl-4'-propoxycarbonyloxymethoxy-biphenyl-4-yl)-acrylic acid; 1-amino-cyclopropanecarboxylic acid 3-adamantan-1-yl-4'-((E)-2-carboxy-vinyl)-biphenyl-4-yl ester and (E)-3-(3'-adamantan-1-yl-4'-cyanomethoxy-biphenyl-4-yl)-acrylic acid.

5. A pharmaceutical composition comprising a compound according to claim 1 and at least one pharmaceutically acceptable excipient diluent.

6. A medicament comprising the pharmaceutical composition of claim 5.

7. A process for synthesizing compounds of formula I wherein A is —CO—, —CH$_2$—(CO)— or —[CO(CHR$^6$)—NH]$_m$—, wherein R$^1$, R$^2$, R$^6$ and w are as defined in claim 1, comprising the following steps:

a) reacting a compound of formula VI

Formula VI wherein R is H or t-Bu, with a compound of formula $R^7$—(CO)—OH, wherein $R^7$—(CO)— has the meaning of $R^1$-$R^2$-A as defined in claim 1, in the presence of a coupling agent and of a base, such base being a tertiary amine; in an aprotic solvent, at a temperature ranging from 0° C. to RT; and b) in case R is t-Bu, cleavage of the tert-butyl ester by means of TFA.

8. A process for synthesizing compounds of formula I wherein $R^1$ is heterocycloalkyl, A is —CO— and $R^2$ is alkylene, comprising the following steps:

a) reacting a compound of formula VI as defined in claim 7, with a halo alkanoyl chloride reagent in the presence of a base, which base being a tertiary amine, in an aprotic solvent, at a temperature ranging from 0° C. to RT; and b) substituting the unreacted halo moiety of the intermediate derivative obtained in step a) with a nucleophilic heterocycloalkyl chosen from the group consisting of pyrrolidine, piperidine, piperazine, morpholine, tetrahydropyran; and c) in case R is t-Bu, cleavage of the tert-butyl ester by means of TFA.

9. A process for synthesizing compounds of formula I wherein $R^1$ is heterocycloalkyl which can be optionally substituted as defined in claim 1, A is —NH(CO)— and $R^1$ and $R^2$ are as defined in claim 1, comprising the following steps:

a) reacting a compound of formula VI as defined in claim 7, with para-nitrophenylchloroformate, in an aprotic solvent in the presence of a base, which base being a tertiary amine, at a temperature ranging from 0° C. to RT; and b) reacting the above obtained intermediate with an amino derivative which may contain further functionalized groups, the latter being optionally protected; and c) in case the above obtained intermediate contains further protected functionalized groups, reacting it appropriately to remove the protecting group.

10. A process for preparing a pharmaceutical composition comprising mixing at least one compound according to claim 1 with a pharmaceutically acceptable salt and/or a pharmaceutically acceptable carrier.

11. A pharmaceutical composition comprising a compound of claim 1, at least one pharmaceutically acceptable excipient and at least one pharmaceutically acceptable diluent.

12. A method for inhibiting the proliferation of carcinoma, lung cancer, or ovarian cancer in a patient in need thereof, the method comprising administering to the patient a therapeutically effective amount of a compound according to claim 1, thereby inhibiting the proliferation of the carcinoma, lung cancer, or ovarian cancer in the patient.

13. The method of claim 12, wherein the carcinoma, lung cancer, or ovarian cancer is metastatic.

14. The method of claim 12, wherein the carcinoma comprises epidermoid carcinoma or metastatic forms thereof.

15. The method of claim 12, wherein the lung cancer comprises non-small cell lung cancer (NSCLC) or metastatic forms thereof.

* * * * *